United States Patent [19]

Broto et al.

[11] Patent Number: 5,476,840
[45] Date of Patent: Dec. 19, 1995

[54] NEW HEXAPEPTIDIC DERIVATIVES, PREPARATION PROCESS AND USE AS MEDICAMENTS OF THESE NEW DERIVATIVES

[75] Inventors: Pierre Broto, Romainville; Giles Hamon, Le Raincy; Eve Mahe; Dung Le-Nguyen, both of Montpellier, all of France

[73] Assignee: Roussel Uclaf, France

[21] Appl. No.: 133,020

[22] PCT Filed: Feb. 11, 1993

[86] PCT No.: PCT/FR93/00145

§ 371 Date: Dec. 3, 1993

§ 102(e) Date: Dec. 3, 1993

[87] PCT Pub. No.: WO93/16104

PCT Pub. Date: Aug. 19, 1993

[30] Foreign Application Priority Data

Feb. 12, 1992 [FR] France ................................ 92 01558

[51] Int. Cl.$^6$ ............................ A61K 38/00; C07K 5/00; C07K 7/00; C07K 17/00
[52] U.S. Cl. .............................................. 514/17; 530/329
[58] Field of Search ................................ 514/17; 530/329

[56] References Cited

U.S. PATENT DOCUMENTS

5,260,276 11/1993 Cody et al. ................................ 514/14

OTHER PUBLICATIONS

Barauy et al. Int. J. Pep. Pnt. Res. vol. 30 p. 705 (1987).
Masaki et al. Med Res. Rev. vol. 12, p. 391 (1992).
Doherty et al. J. Cardiovascular Pharm. vol. 17 pp. 559–561 (1991).
Greenlee et al. Pharm. Res. vol. 4, p. 364 (1987).

*Primary Examiner*—Jill Warden
*Assistant Examiner*—Sheela J. Huff
*Attorney, Agent, or Firm*—Bierman and Muserlian

[57] ABSTRACT

New peptidic derivatives having the general formula (I): $X_1$ $X_2$ $X_3$ Ile $X_5$ $X_6$ wherein $X_1$ is hydrogen, a rest of histidin, of acetyl-histidin or of D-histidin, $X_2$ is a rest of alanin, of leucin, of tryptophan, of phenylalanin as well as their homologs in D series, $X_3$ is a rest of alanin as well as its D series homolog, $X_5$ is a rest of isoleucin, of alanin, of valin, of norleucin, of leucin and of aspanic acid as well as their D series homologs, $X_6$ is a rest of tryptophan, of leucin, of isoleucin, of norleucin and their D series homologs, method for the preparation and application of such new derivatives as medicaments.

7 Claims, No Drawings

NEW HEXAPEPTIDIC DERIVATIVES, PREPARATION PROCESS AND USE AS MEDICAMENTS OF THESE NEW DERIVATIVES

The present application relates to new hexapeptide derivatives, the preparation process and the use as medicaments of these new derivatives.

It is known that endothelin is a powerful vasoconstrictor extracted from porcine aortic endothelium. This peptide, which has been isolated recently, contains 21 amino acids, has 2 disulphide bridges and has the following formula:

Cys—Ser—Cys—Ser—Ser—Leu—Met—Asp—Lys—Glu—Cys—Val—Tyr—Phe—Cys—His—Leu—Asp—Ile—Ile—Trp
1            5                                              10                                15                              20

(—A novel potent vasoconstrictor peptide produced by vascular endothelial cells. M. Yanagisawa, H. Kurihara, S. Kimura, Y. Tomobe, M. Kobayashi, Y. Mitsui, Y. Yazaki, K. Goto & T. Masaki, Nature, (1988) 332, pp. 411–415). This peptide is designated in what follows under the name of ET1.

The nomenclature used is that of the IUPAC-IUB commission (1984) European J. Biochem 183, 9–37.

This peptide, which contains 21 amino acid residues, 2 disulphide bridges, is capable of contracting at very low doses the smooth muscle cells (arteries and veins) of various types of mammals (man, dog, cat, pig, guinea pig, rat, rabbit . . . ). By trying to shorten the chain and replace certain amino acid residues of endothelin by other amino acids, the Applicant prepared by synthesis new hexapeptide derivatives containing only five or six amino acids in which the vasoconstrictive activity has practically disappeared and which furthermore have the property of blocking and fixing themselves on the natural receptors of endothelin. The products therefore present an activity which will oppose any subsequent action for releasing endothelin.

In addition, these products are of interest because they can be prepared by total synthesis in large quantities.

Therefore a subject of the present Application is new hexapeptide derivatives corresponding to the general formula (I):

$$X_1\text{-}X_2\text{-}X_3\text{-}Ile\text{-}X_5\text{-}X_6 \qquad (I)$$

in which
$X_1$ represents a hydrogen atom or a residue of histidine, acetyl-histidine, or D-histidine,
$X_2$ represents a residue of alanine, leucine, tryptophan, phenylalanine as well as their D series equivalents,
$X_3$ represents an alanine residue as well as its D series equivalent,
$X_5$ represents a residue of isoleucine, alanine, valine, norleucine, leucine and aspartic acid as well as their D series equivalents,
$X_6$ represents a residue of tryptophan, leucine, isoleucine, norleucine and their D series equivalents.

Among the new hexapeptide derivatives, as defined above, there are particularly preferred those characterized in that:
$X_1$ represents a hydrogen atom, a histidine or D-histidine residue,
$X_2$ represents an alanine or leucine residue, as well as their D series equivalents,
$X_3$ represents an alanine residue as well as its D series equivalent,
$X_5$ represents an isoleucine residue as well as its D series equivalent,
$X_6$ represents a tryptophan residue, as well as its D series equivalent.

Among these, there are preferred the peptide derivatives in which:
$X_1$ represents a hydrogen atom or a histidine residue,
$X_2$ represents an alanine residue,
$X_3$ represents an alanine or aspartic acid residue,
$X_5$ represents an isoleucine residue,
$X_6$ represents a tryptophan or D-tryptophan residue.

Among the preferred new hexapeptide derivatives of the invention, there is more particularly preferred one of the following peptide derivatives:

| | |
|---|---|
| His—Ala—Ala—Ile—Ile—Trp,<br>1                           5 | Sequence ID No. 1 |
| Leu—Ala—Ile—Ile—Trp,<br>1                   5 | Sequence ID No. 2 |
| His—Leu—Ala—Ile—Ile—D Trp,<br>1                           5 | Sequence ID No. 3 |
| Leu—Ala—Ile—Ile—D Trp,<br>1                   5 | Sequence ID No. 4 |
| Ala—Ala—Ile—Ile Trp,<br>5                   5 | Sequence ID No. 5 |

Among the new hexapeptide derivatives as defined above, the following peptide derivative is quite particularly preferred:

| | |
|---|---|
| His—Ala—Ala—Ile—Ile—Trp,<br>1                           5 | Sequence ID No. 1 |

Also a subject of the invention is a preparation process for the new hexapeptide derivatives as defined above, characterized in that a solid-phase synthesis is carried out by sequentially introducing the duly-protected amino acids on a support of cross-linked polystyrene type, using a coupling agent, the amino acids are deprotected, and the peptide chain thus formed is released from the resin, in order to obtain the peptide derivative of formula (I) thus sought.

In the preferred implementation conditions, the process described above is characterized in that:
the support of cross-linked polystyrene type is a resin of "Boc-Trp-CM" type or "Boc-D-Trp-CM" type in which Boc is a tertiobutyloxycarbonyl group, Trp is a tryptophyl group and D- Trp is a D-tryptophyl group and CM designates the cross-linked polystyrene support,
the coupling agent is (benzotriazol-1-yloxy) tris(dimethylamino) phosphonium hexafluorophosphate or Bop,
the release of the peptide chain from the support as well as the deprotection of the amino acids is carried out using hydrofluoric acid operating at low temperature, preferably at about 0° C.

The new hexapeptide derivatives which are a subject of the present invention have very useful pharmacological properties; in particular a remarkable, practically pure antagonistic effect against hypertension caused by endothelin and an anti-ischemic effect, the vasoconstrictive activity of endothelin being abolished, are noted.

Some of these properties are illustrated further on in the experimental part.

These properties justify the use of the new hexapeptide derivatives corresponding to formula (I) above as medicaments.

Therefore a subject of the present invention is also the use as medicaments of the new hexapeptide derivatives as defined by general formula (I) above.

Among the medicaments which are a subject of the invention, there are in particular preferred the medicaments, characterized in that they are constituted by the products of formula (I) in which $X_1$ represents a hydrogen atom, a histidine or D-histidine residue, $X_2$ represents an alanine or leucine residue, as well as their D series equivalents, $X_3$ represents an alanine residue, as well as its D series equivalent, $X_5$ represents an isoleucine residue, as well as its D series equivalent, $X_6$ represents a tryptophan or D-tryptophan residue.

Among these, there are preferred the medicaments containing the new peptide derivatives as defined above, in which:

$X_1$ represents a hydrogen atom or a histidine residue,
$X_2$ represents an alanine or leucine residue,
$X_3$ represents an alanine residue,
$X_5$ represents an isoleucine residue,
$X_6$ represents a tryptophan or D-tryptophan residue.

Among the preferred medicaments of the invention, there are more particularly preferred those constituted by one of the following peptide derivatives:

| | |
|---|---|
| His Ala Ala Ile Ile Trp,<br>1       5 | SEQ ID NO: 3 |
| Leu Ala Ile Ile Trp,<br>1       5 | SEQ ID NO: 4 |
| His Leu Ala Ile Ile D Trp,<br>1       5 | SEQ ID NO: 5 |
| Leu Ala Ile Ile D Trp,<br>1       5 | SEQ ID NO: 6 |
| Ala Ala Ile Ile Trp.<br>1       5 | SEQ ID NO 7 |

Among the medicaments of the invention, the following peptide derivative is quite particularly preferred:

| | |
|---|---|
| His Ala Ala Ile Ile Trp.<br>1       5 | SEQ ID NO: 3 |

These medicaments can be used, for example, in the treatment of all vascular spasms, in the treatment of cerebral post-haemorrhages, in the treatment of coronary spasms, peripheral vascular spasms as well as in the treatment of renal insufficiencies. These medicaments can also be used in the treatment of myocardial infarction, in the prevention of post-angioplastic recurrence of stenosis, in the treatment of atherosclerosis, certain forms of hypertension, as well as in the treatment of asthma.

The usual dose, variable according to the product used, the patient being treated and the affection in question, can be for example from 1 to 300 mg per day by intravenous route in man.

Also a subject of the invention is the pharmaceutical compositions which contain at least one previously-mentioned derivative as active ingredient.

As active ingredient, the peptide derivatives corresponding to general formula (I) can be incorporated in the pharmaceutical compositions intended for digestive or parenteral route.

These pharmaceutical compositions can be, for example, solid or liquid and can be presented in the pharmaceutical forms commonly used in human medicine, such as for example, plain or sugar-coated tablets, gelules, capsules, granules, suppositories, injectable preparations, aerosols; they are prepared according to the usual methods. The active ingredient or ingredients can be incorporated with the excipients usually employed in these pharmaceutical compositions, such as talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agent, preservatives.

Non-limitative examples of the implementation of the invention will now given.

EXAMPLE 1

| | |
|---|---|
| His Ala Ala Ile Ile Trp<br>1       5 | SEQ ID NO: 3 |

STAGE A

Assembly of the Peptide Chain

A support of "Boc-Trp-CM-support" type is used in which Boc is a tertiobutyloxycarbonyl group, Trp represents a tryptophyl group and CM-support designates the cross-linked polystyrene support.

The support containing 0.6 mmol Trp/g was prepared by the potassium fluoride method according to the technique described by Horiki K., Igano K. & Inouye K. (1978) Chemistry Lett., 165–168.

All the amino acids are N-protected by the tertiobutylcarbonyl group, the protective groups of the side chains were the following:
cyclohexyl ester for the aspartic acid,
Nim-tertiobutyloxycarbonyl for the histidine,
the tryptophan is not protected.

Coupling reactions were carried out using Bop or (benzotriazol-1-yloxy tris (dimethylamino) phosphonium hexafluorophosphate.

A coupling cycle can be summarized as follows:
Deprotection:
1—Treatment with a solution of trifluoroacetic acid (50%) in dichloromethane containing 3% ethanedithiol for one minute.
2—Draining then treatment with a 50% trifluoroacetic acid solution in dichloromethane containing 3% ethanedithiol for 30 minutes.
3—Draining then washing with isopropanol containing 5% ethanedithiol.
4—Washing with dichloromethane, twice.
Coupling:
1—Addition of Bop and Boc - amino acid.
2—Addition of diisopropylethylamine (6 equivalents) then of solvent (dichloromethane or dimethylformamide) under agitation.

3—After negative reaction to ninhydrin, washing twice with dichloromethane.

Control tests using ninhydrin were carried out according to the the process described by Kaiser, E., Colescott, R. L., Bossinger, C. D. & Cook, P. I. (1970) Anal. Biochem. 24, 595–598.

Before treatment with hydrofluoric acid the last Boc group is eliminated with trifluoroacetic acid.

From 1 g of "Boc-Trp-CM-resin" resin 1.5 g of protected peptide chain - resin complex is thus obtained operating manually, which resin is used directly in the following stage.

STAGE B

Release of the Protected Peptide Chain - Resin Complex 1.5 g of protected peptide chain - resin complex is reacted for 60 minutes with 15 ml of hydrofluoric acid at 0° C. in the presence of anisole (1 ml). The resin is washed with ether; the crude peptide is extracted with a 20% aqueous solution of acetic acid. After lyophilization, 250 mg of crude product is obtained.

The fraction obtained is lyophilized and finally 30 mg of expected product is collected.

EXAMPLES 2 TO 5

By operating in the same manner as in Example 1, but with other amino acids, the other peptides which appear hereafter were prepared.

| EXAMPLE 2: | Leu Ala Ile Ile Trp SEQ ID NO:4 |
|---|---|
| | 1                              5 |
| EXAMPLE 3: | His Leu Ala Ile Ile D Trp SEQ ID NO:5 |
| | 1                                          5 |
| EXAMPLE 4: | Leu Ala Ile Ile D Trp SEQ ID NO:6 |
| | 1                                    5 |
| EXAMPLE 5: | Ala Ala Ile Ile Trp. SEQ ID NO:7 |
| | 1                                5 |

Each product of Examples 1 to 5 was sequenced and its mass was checked by mass spectrometry.

EXAMPLE 6

An injectable solute was prepared corresponding to the following formulation:

| product of Example 1 | 1 mg |
|---|---|
| aqueous sterile excipient | 2 ml |

EXAMPLE 7

Tablets were prepared corresponding to the following formula:

| product of Example 1 | 2 mg |
|---|---|
| excipient, sufficient quantity for a tablet completed at | 150 mg |

(composition of the excipient: lactose, starch, talc, magnesium stearate).

STUDY OF THE ACTIVITY ON THE ENDOTHELIN RECEPTOR

A membrane preparation was made from rat posterior cortex plus cerebellum. The tissue is homogenized with a POLYTRON in a 50 mM Tris pH=7.4 buffer.

After 30 minutes at 25° C. (W.B.) the homogenate is centrifuged at 30000 g for 15 minutes (2 centrifugings with intermediate take-up in the Tris pH. 7.4 buffer).

The pellets are put in suspension in an incubation buffer (25 mM Tris, 5 microg/ml pepstatin A, 3 microg/ml aprotinin, 0.1 mM PMSF, 3 mM EDTA, 1 mM EGTA pH 7.4).

Aliquots of 2 ml are distributed into hemolysis tubes and $^{125}$I endothelin (approximately 50000 dpm/tube) and the product to be studied are added. (The product is first tested at $3\times10^{-5}$M three times). When the product tested displaces more than 50% of the radioactivity bound specifically to the receptor, it is tested again according to a range of 7 concentrations so as to determine the concentration which inhibits by 50% the radioactivity bound specifically to the receptor. In this way the 50% inhibiting concentration is determined.

The non-specific bond is determined by the addition of endothelin at $10^{-6}$M (three times). Incubation is carried out at 25° C. for 60 minutes, the product is put back in a water-bath at 0° C., for 5 minutes, followed by filtration under reduced pressure and rinsing with Tris 7.4 buffer, and the radioactivity is counted in the presence of scintillating Triton.

The result is expressed directly as a 50% inhibiting concentration ($IC_{50}$), that is to say as the concentration of studied product expressed in nM necessary to displace by 50% the specific radioactivity fixed on the receptor studied.

RESULT

The IC50's found for the products of Examples 1 and 2 are given in table I hereafter, in nanomoles.

TABLE 1

| EXAMPLES | IC 50 |
|---|---|
| 1 | 100,000 |
| 2 | 100,000 |

STUDY OF THE VASOCONSTRICTIVE ACTIVITY AND OF THE ANTAGONISM OF THE EFFECTS OF ENDOTHELIN IN A DEMEDULLATED RAT

Male Sprague-Dawley rats are anaesthetized with Nembutal (60 mg/kg) injected by intraperitoneal route. The animals are then demedullated, put under assisted respiration (1 ml/100 g—50 insufflations per minute), then the vagus nerves are sectioned. A carotid artery is catheterized to record the arterial pressure and the products to be studied are injected into the pudendal vein.

Study of the Vasconstrictive Activity

The animals receive endothelin 1 or the compound to be tested as cumulative injections by venous route, the administrations being spaced 2 minutes apart.

The increase in mean arterial pressure (MAP) induced by each compound is measured and expressed as a percentage variation relative to the initial pressure.

Study of the Antagonistic Activity of Endothelin

Ten minutes after the intravenous injection of the solvent or compounds to be tested, the animals receive administrations of endothelin 1 in a cumulative manner (1, 3, 10 and 30 µg/kg i.v.) every 2 minutes.

The antagonistic activity is expressed as a percentage of the inhibition of the pressure response to endothelin administered alone, at doses of 3 and 10 µg/kg.

RESULTS

The vasoconstrictive activity of the compound of Example 1 is given in Table II hereafter:

TABLE II

| Example | Doses (mg/kg) | % increase of MAP |
|---------|---------------|-------------------|
| 1       | 10            | +8%               |

The antagonist activity of the compound of Example 1 is given in Table III hereafter:

TABLE III

| Example | Doses (µg/kg) | Percentage of inhibition of the responses to endothelin | |
|---------|---------------|---------------------|---------------------|
|         |               | 3 µg endothelin     | 10 µg endothelin    |
| 1       | 5             | −27                 | −19                 |
|         | 10            | −60                 | −33                 |

We claim:

1. A hexapeptide of the formula $$X_1\text{-}X_2\text{-}X_3\text{-}Ile\text{-}X_5\text{-}X_6 \qquad I$$

in which $X_1$ is hydrogen atom or a histidine residue,
$X_2$ is an alanine residue or its D series equivalents,
$X_3$ is an alanine residue, or its D series equivalents,
$X_5$ is an isoleucine residue or its D series equivalents,
$X_6$ is a tryptophan or D-tryptophan residue.

2. A hexapeptide of claim 1 having the formula

```
        His Ala Ala Ile Ile Trp.
        1               5
```

3. A process for the preparation of hexapeptides of claim 1 comprising solid-phase synthesis, wherein said solid-phase synthesis is carried out by sequentially coupling duly-protected amino acids to a support of cross-linked polystyrene resin using a coupling agent, deprotecting the amino acids, forming a hexapeptide chain and releasing the formed hexapeptide chain from the resin to obtain the hexapeptide of claim 1.

4. Process according to claim 3 wherein
the support of cross-linked polystyrene is a resin of "Boc-Trp-CM" or "Boc-D-Trp-CM" in which Boc is a tertiobutyloxycarbonyl group, Trp is a tryptophyl and D-Trp is a D-tryptophyl and CM is the cross-linked polystyrene support,
the coupling agent is (benzotriazol-1-yloxy) tris(dimethylamino) phosphonium hexafluorophosphate or Bop,
the release of the peptide chain from the support as well as the deprotection of the amino acids is carried out using hydrofluoric acid operating at low temperature.

5. An anti-hypertension composition comprising an anti-hypertensively effective amount of at least one hexapeptide of claim 1 and an inert pharmaceutical carrier.

6. A method of inducing anti-hypertensive activity in warm-blooded animals comprising administering to warm-blooded animals an anti-hypertensively effective amount of a hexapeptide of claim 1.

7. A hexapeptide of claim 1 selected from the group consisting

```
        His—Ala—Ala—Ile—Ile—Trp, and
        1                   5

Ala—Ala—Ile—Ile—Trp.
        1               5
```

* * * * *

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 21
        ( B ) TYPE: AMINO ACID
        ( D ) TOPOLOGY: UNKNOWN ( i i ) MOLECULE TYPE:
        ( A ) DESCRIPTION: PEPTIDE ( x i ) SEQUENCE DESCRIPTION:SEQ ID NO:1:

```
Cys  Ser  Cys  Ser  Ser  Leu  Met  Asp  Lys  Glu  Cys  Val  Tyr  Phe
1                   5                        10
Cys  His  Leu  Asp  Ile  Ile  Trp
15                   20
```

( 2 ) INFORMATION FOR SEQ ID NO:2:

( i ) SEQUENCE CHARACTERISTICS:
        ( A ) LENGTH: 6
        ( B ) TYPE: AMINO ACID
        ( D ) TOPOLOGY: UNKNOWN ( i i ) MOLECULE TYPE:
        ( A ) DESCRIPTION: PEPTIDE ( v ) FEATURE:
        ( A ) NAME/KEY:
        ( B ) LOCATION:
        ( C ) IDENTIFICATION METHOD:
        ( D ) OTHER INFORMATION: Amino acid 1
            ( X a a ) is hydrogen, histidine,
            acetyl- histidine, or D-histidine;
            amino acid 2 (Xaa) is alanine,
            leucine, tryptophan, phenylalanine,
            D-alanine, D- leucine, D-tryptophan,
            or D- phenylalanine; amino acid 3
            ( X a a ) is alanine or D-alanine; amino
            acid 5 (Xaa) is isoleucine, alanine,
            valine, norleucine, leucine, 5,476,840

9

10

-continued aspartic acid, D-isoleucine,
D-alanine, D- valine, D-norleucine,
D-leucine, or D-aspartic acid; amino
acid 6 (Xaa) is tryptophan, leucine,
isoleucine, norleucine, D-
tryptophan, D-leucine, D-
isoleucine, or D-norleucine.

( x i ) SEQUENCE DESCRIPTION:SEQ ID NO:2:

```
Xaa  Xaa  Xaa  Ile  Xaa  Xaa
1                 5
```

( 2 ) INFORMATION FOR SEQ ID NO:3:

( i ) SEQUENCE CHARACTERISTICS:
        ( A ) LENGTH: 6
        ( B ) TYPE: AMINO ACID
        ( D ) TOPOLOGY: UNKNOWN ( i i ) MOLECULE TYPE:
        ( A ) DESCRIPTION: PEPTIDE ( x i ) SEQUENCE DESCRIPTION:SEQ ID NO:3:

```
His  Ala  Ala  Ile  Ile  Trp
1                 5
```

( 2 ) INFORMATION FOR SEQ ID NO:4:

( i ) SEQUENCE CHARACTERISTICS:
        ( A ) LENGTH: 5
        ( B ) TYPE: AMINO ACID
        ( D ) TOPOLOGY: UNKNOWN ( i i ) MOLECULE TYPE:
        ( A ) DESCRIPTION: PEPTIDE ( x i ) SEQUENCE DESCRIPTION:SEQ ID NO:4:

```
Leu  Ala  Ile  Ile  Trp
1                 5
```

( 2 ) INFORMATION FOR SEQ ID NO:5:

( i ) SEQUENCE CHARACTERISTICS:
        ( A ) LENGTH: 6
        ( B ) TYPE: AMINO ACID
        ( D ) TOPOLOGY: UNKNOWN ( i i ) MOLECULE TYPE:
        ( A ) DESCRIPTION: PEPTIDE ( v ) FEATURE:
        ( A ) NAME/KEY:
        ( B ) LOCATION:
        ( C ) IDENTIFICATION METHOD:
        ( D ) OTHER INFORMATION: Amino acid 6
        ( X a a ) is D- tryptophan.

( x i ) SEQUENCE DESCRIPTION:SEQ ID NO:5:

```
His  Leu  Ala  Ile  Ile  Xaa
1                 5
```

( 2 ) INFORMATION FOR SEQ ID NO:6:

( i ) SEQUENCE CHARACTERISTICS:
        ( A ) LENGTH: 5
        ( B ) TYPE: AMINO ACID
        ( D ) TOPOLOGY: UNKNOWN ( i i ) MOLECULE TYPE:
        ( A ) DESCRIPTION: PEPTIDE ( v ) FEATURE:
  ( A ) NAME/KEY:
  ( B ) LOCATION:
  ( C ) IDENTIFICATION METHOD:
  ( D ) OTHER INFORMATION: Amino acid 5
  ( X a a ) is D- tryptophan.

( x i ) SEQUENCE DESCRIPTION:SEQ ID NO:6:

```
        Leu   Ala   Ile   Ile   Xaa
        1                       5
```

( 2 ) INFORMATION FOR SEQ ID NO:7:

( i ) SEQUENCE CHARACTERISTICS:
    ( A ) LENGTH: 5
    ( B ) TYPE: AMINO ACID
    ( D ) TOPOLOGY: UNKNOWN ( i i ) MOLECULE TYPE:
    ( A ) DESCRIPTION: PEPTIDE ( x i ) SEQUENCE DESCRIPTION:SEQ ID NO:7:

```
        Ala   Ala   Ile   Ile   Trp
        1                       5
```